United States Patent [19]

Fletcher

[11] Patent Number: 5,082,370
[45] Date of Patent: Jan. 21, 1992

[54] INDUSTRIAL COLORIMETER HAVING LIGHT INTENSITY COMPENSATION MEANS

[75] Inventor: Thomas A. Fletcher, Freeport, Ill.
[73] Assignee: Honeywell Inc., Minneapolis, Minn.
[21] Appl. No.: 538,362
[22] Filed: Jun. 14, 1990
[51] Int. Cl.$^5$ ............................................. G01J 3/42
[52] U.S. Cl. ................................... 356/328; 364/526
[58] Field of Search ............... 356/319, 326, 328, 402, 356/406, 407, 408, 416, 419, 425; 364/526, 498

[56] References Cited
U.S. PATENT DOCUMENTS 4,076,421 2/1978 Kishner ............................... 356/236
4,449,821 5/1984 Lee ...................................... 356/319

Primary Examiner—F. L. Evans
Attorney, Agent, or Firm—Robert B. Leonard

[57] ABSTRACT

A colorimeter provides compensation for changes in the color signature of an object due to lamp aging, stand off distance and view angle changes. The colorimeter senses and stores values indicative of a sample object. In use, the colorimeter senses and creates values indicative of an object. The colorimeter includes a processor which then creates an average ratio wherein the stored values and corresponding sensed values are placed in a ratio, all of the ratios are then summed, and the total is divided by the number of values. Finally, the processor compares the sensed values with corresponding stored values, wherein one of the two values is adjusted by the average ratio.

18 Claims, 3 Drawing Sheets

INDUSTRIAL COLORIMETER HAVING LIGHT INTENSITY COMPENSATION MEANS

BACKGROUND OF THE INVENTION

This invention is directed towards the field of color signature sensors used in process automation. More specifically, the invention is a method and an apparatus which performs color recognition of objects for the purposes of identification, sorting or matching.

Colorimeters are well known devices used for characterizing the color of an object and comparing the color of an object to the color of other objects. A lamp, either in the colorimeter or an external source, provides illumination which is reflected or transmitted by the object to a device which disperses light into an array of wavelength components. A detector array then converts the array of wavelength components into discrete signals which are representative of a color signature of the object. The discrete signals are then sent to an analog to digital converter and then on to a processor for processing. Processing involves a component by component subtraction of sensed component values from stored component values to produce a relative signature difference. Generally, as long as the relative signature difference falls within predetermined limits, the color of the sensed object will be acceptable.

This method of color differentiation is very accurate as long as the standoff distance, view angle and ambient lighting are held constant. However, in most industrial applications, it is not feasible to tightly control the presentation of the object to the colorimeter or the lighting of the object.

Another problem associated with colorimeters is that as the illuminating lamp ages, the color and intensity of the light produced by the lamp can change. This, in turn, causes the color signature of a sensed object to vary with the age of the lamp. This variation in color signature may result in many acceptable pieces being discarded due to erroneous color sensing.

One attempted solution to the problem of lamp aging is to increase the lamp voltage as the lamp ages in order to maintain a constant intensity and color output. However, it has been shown that changing the lamp voltage significantly affects lamp life.

$$(life_{actual}/life_{design}) = V_{design}/V_{actual})^{10 \sim 14}$$

This means that a voltage increase of five percent will result in an approximate reduction in life of fifty percent.

Another possible solution to the problem of lamp aging is frequent recalibration of the colorimeter. However, this is only feasible in a laboratory environment. In commercial environments, access to the colorimeter may be difficult. Further, frequent recalibration increases the costs of scanning.

Thus, it is an object of the present invention to provide a colorimeter which compensates for changes in lighting, view angle and standoff distance. It is a further object of the present invention to provide colorimetric sensing which compensates for lamp aging without adversely affecting lamp life. It is yet another object of the present invention to provide colorimetric sensing which compensates for lamp aging without requiring frequent recalibration.

SUMMARY OF THE INVENTION

The present invention is a method and apparatus for eliminating the effects of lighting, view angle, standoff distance and lamp aging in colorimetric sensing. The inventive colorimeter comprises a lamp, a diffraction grating for separating light into its component wavelengths, a detector array for sensing the component wavelengths and a processor which includes a compensation means. The processor compares sensed component values with stored component values to produce a signature difference or DELTA. The compensation means causes the stored component value to be adjusted by a factor based on an average of the ratios of sensed wavelength component values and corresponding stored wavelength component values.

DETAILED DESCRIPTION OF THE PREFERRED EMBODIMENT

Figure 1:
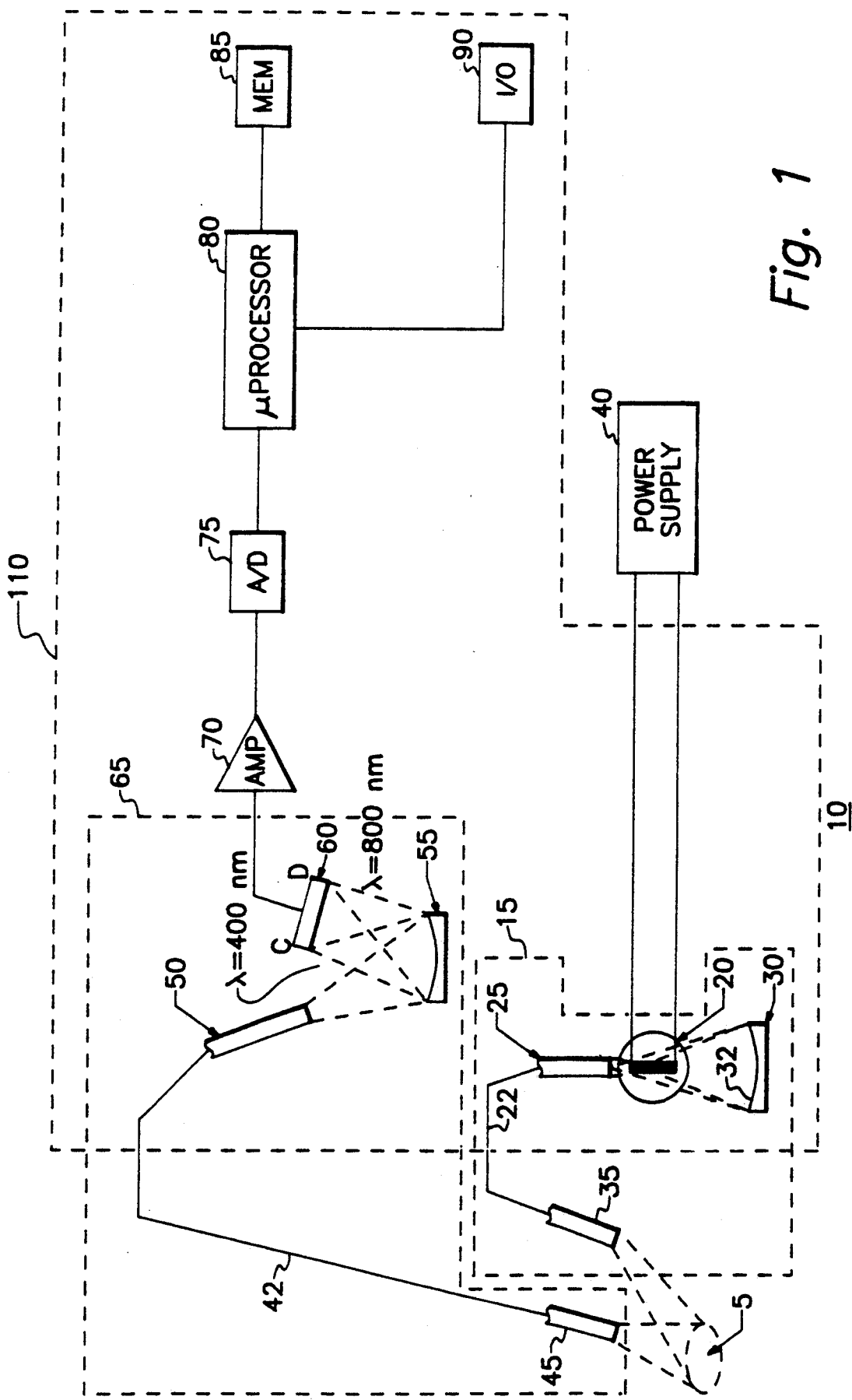
FIG. 1 is a block diagram of the inventive colorimeter and an object to be analyzed.

A preferred embodiment of the inventive colorimeter is shown in FIG. 1. The colorimeter 10 is used to detect the color signature of an object 5.

Lighting means 15 is used to illuminate object 5. In one implementation, lighting means 15 comprises a lamp 20, a mirror 30 and optical fiber 22. Lamp 15 is generally a halogen incandescent lamp. Power supply 40 is connected to lamp 15 to provide electrical power.

First optical fiber 22 is used to transmit light from lamp 20 to object 5. First optical fiber 22 has two ends, a light receiving end 25 positioned near lamp 20 and a light exiting end 35 positioned near a location where objects such as object 5 to be analyzed.

Mirror 30 is positioned near lamp 20 opposite light receiving end 25. Mirror 30 has a concave side 32 which faces the lamp 20 and focuses light on the light receiving end of optical fiber 22. Use of such a mirror and first optical fiber is optional, but by using the mirror in first optical fiber an increase light intensity may be transmitted to the object. Collectively, the mirror and the first optical fiber are known are light focusing means.

Object 5 will generally reflect or transmit a portion of the light transmitted to it by illumination means 15. The amount of and composition of the reflected or transmitted light depends upon the surface and color of the object. For this description, only reflected light will be discussed although for the present purposes the two terms are interchangeable. The reflected light will be carried by a second optical fiber 42 from object 5 to a dispersing element 55. Second optical fiber 42 has two ends, light receiving end 45 positioned near the object and a light exiting end 50. Reflected light leaving light exiting end 50 strikes dispersing element 55. Dispersing element 55 may be a diffraction grating. The reflected light is then broken into its component wavelengths and reflected to detector array 60. For this embodiment, dispersing element 55 disperses and provides a flat field focus of the spectrum (400 nm to 800 nm) and provides a flat field focus of the spectrum (400 nm to 800 nm) on detector array 60. The focused spectrum strikes array detector 60 with 400 nm light at side C and 800 nm light at side D.

The light dispersed and reflected by dispersing element 55 is directed toward a detector array 60. Detector array 60 may be comprised of a linear sequence of photodetectors. Each photodetector is adapted to produce an electrical signal when light of a predetermined frequency impinges thereon. The magnitude of the signal is directly proportional to the intensity of the light which strikes the photodetectors. A convenient shorthand notation for the second optical fiber, the dispersing element and the detector array is a sensing means 65.

The detector array produces an analog signal indicative of the color signature of object 5. The analog signal is amplified by amplifier 70 and then digitized by A/D converter 75 thus creating an array of sensed wavelength component values. After digitization, the array of sensed wavelength component values is sent to processor 80 for processing.

Processing of the array of sensed wavelength component values involves a comparison between each of the components of the array and each component of a stored component array. The stored component array is a base line color signature to which all sensed objects will be compared. The colorimeter is "trained" before it is used by having the sensing means sense, digitize and store color information from a sample object. The sample object must have the surface and color desired of all the objects to be analyzed. The stored component array is stored in memory 85. Selection of a mode of operation for the colorimeter can be controlled by input/output controller 90.

Figure 3:
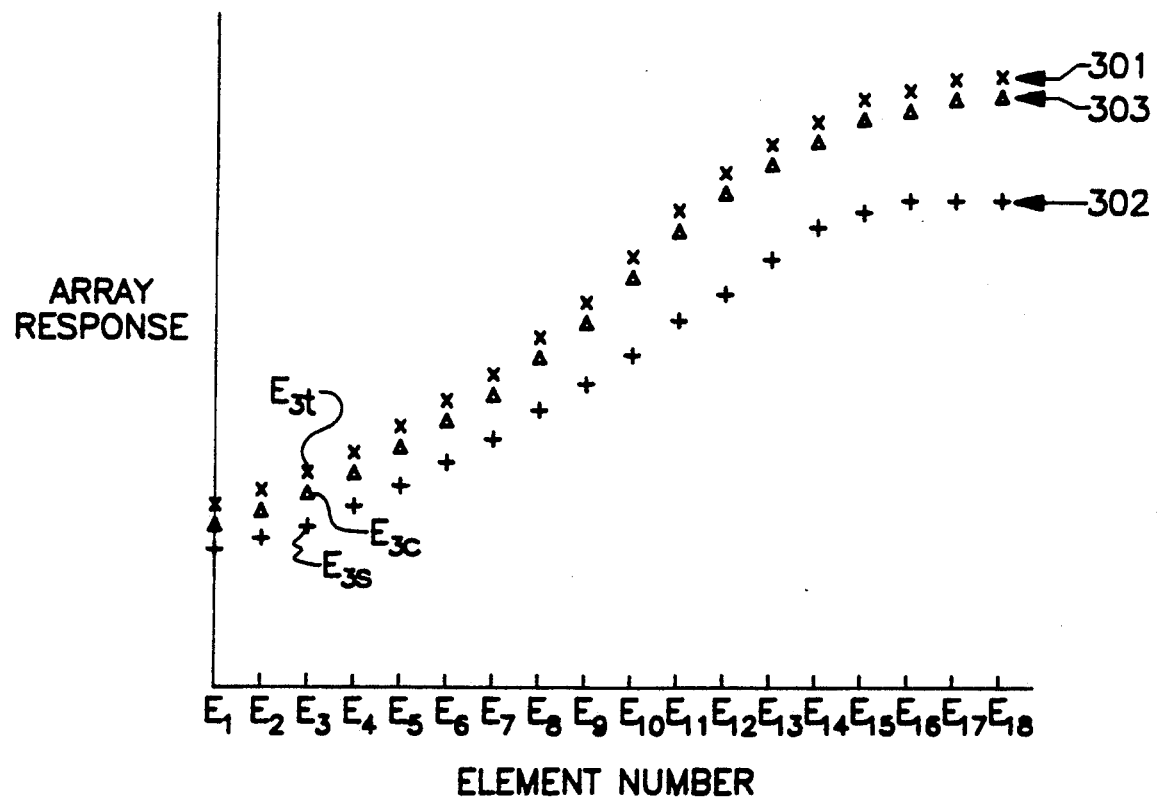
FIG. 3 is comparison between a stored color signature and the sensed color signature with and without compensation.

As was already suggested, each of the values of the sensed component array is compared with a corresponding component from the stored component array. This can be better understood with reference to FIG. 3. In FIG. 3, curve 301 is representative of the color signature which is stored during the training of the sensor. Curve 302 is the sensed component wavelength array from an object that has been scanned. Looking at one representative component, processor 80 begins by determining the difference between each of the stored component values and the sensed component wavelength values. For example, the processor 80 would subtract the sensed component values $E_{3S}$ from stored component values $E_{3T}$ to produce a DELTA. If the calculated DELTA fell outside predetermined limits, the object which produced this color signature would be deemed to have an unacceptable color and thus would be discarded. However, this DELTA may in part be due to aging of the lamp, view angle or stand off distance.

In order to explain the compensation method and means of the present invention, a further understanding of the problem is necessary. To describe the effects of the intensity compensation algorithm, the terms hue, value and chroma will be used. While the data provided to the processor 80 of the colorimeter contains more information than just hue, value and chroma, these terms are commonly used to describe color. Hue can be described as the dominant wavelength of the light. Value can be described as the gray scale or lightness of a color. Chroma describes the saturation or how vivid a color appears. It has been determined that a change in illustration caused by variations in standoff, view angle or lighting (including lamp aging) represent changes in value. As a result, the present invention attempts to eliminate effects of value changes on the color matching algorithm.

Figure 4A:
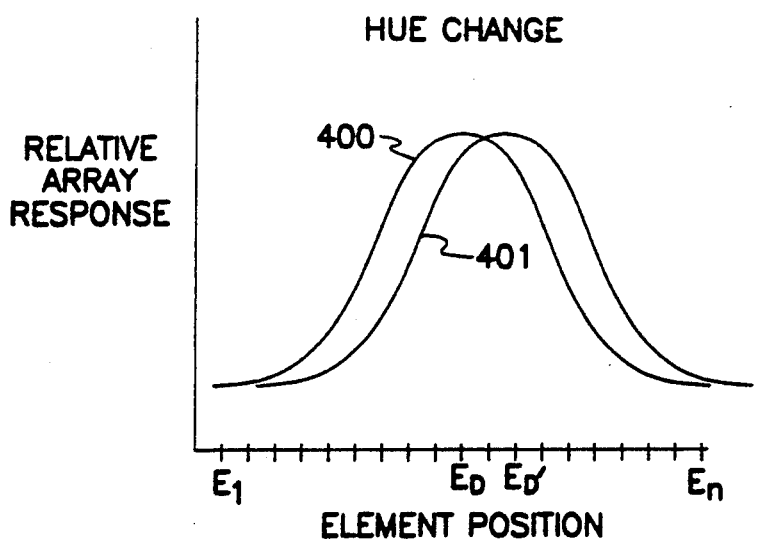
FIGS. 4a-c show the effects of a shift in hue, value or chroma respectively on a color signature curve.
Figure 4B:
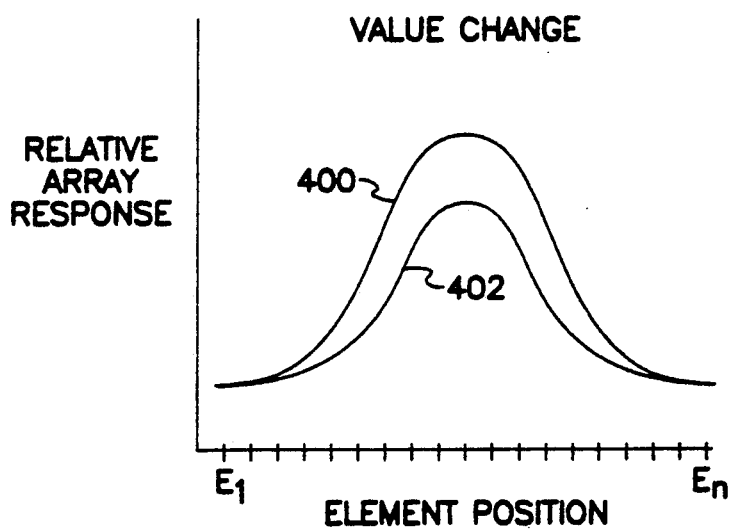
Figure 4C:
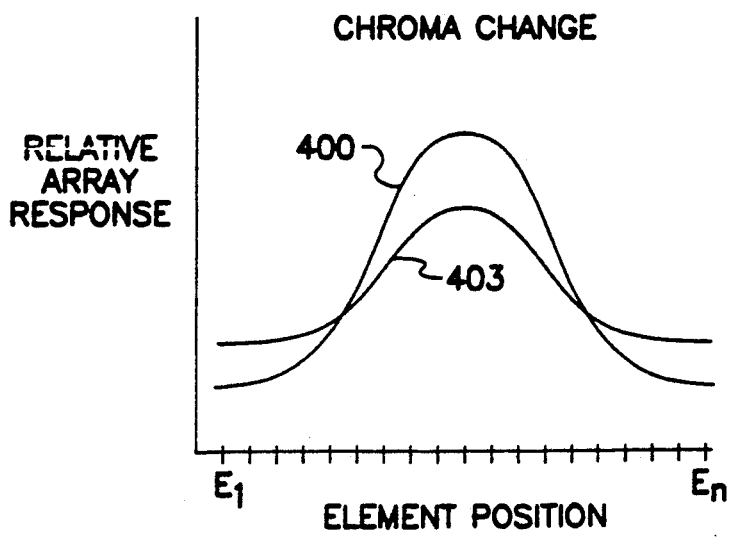

Turning now to FIGS. 4a, 4b and 4c, there shown are curves representing a baseline color signature of a light, and curves showing the effects of a change in hue, value and chroma. FIG. 4a shows the effects of a hue change. Curve 400 represents a base line curve. Curve 401 shows the effect on curve 400 of a hue only change. Notice that the dominant wavelength $E_D$ has shifted to $E_{D'}$, while the peak responses for curve 401 stays the same as curve 400.

In FIG. 4b, baseline curve 400 undergoes a change in value to produce curve 402. Note that curve 402 has the same dominant wavelength and shape as curve 401, but has a different peak value. Changes in values are described mathematically as simply of the base curve multiplied by a multiplier.

In FIG. 4c, baseline curve 400 undergoes a chroma change to produce curve 403. A chroma change results in a change in the shape of the curve.

Because a change in light intensity results primarily in a change in value, compensation for an intensity change involves determination of and correction for the multiplier. The compensation means corrects for this multiplier and calculates a signature difference by using the following formula:

$$\Sigma |E_s - E_t (\Sigma(E_s/E_t)/N_e)| = \text{Delta}$$

where
$E_s$ = sensed component wavelength values
$E_t$ = stored component values
$N_e$ = total number of components (determined by the number of discrete signals from the array detector
Average Ratio = $\Sigma(E_s/E_t)/N_e$
Delta = relative signature difference The average ratio is determined first. Each $E_s$ is divided by a corresponding $E_t$ and added to a sum of earlier ratios. After all of the ratios have been calculated and summed, the product is then divided by the number of components. After the average ratio is determined, the Delta can be calculated as shown.

An alternative compensation mean multiplies the sensed wavelength component values by a second average ratio. The stored component values are then subtracted from the product to produce Delta:

$$\Sigma |E_t - E_s (\Sigma(E_t/E_s)/N_e)\Sigma = \text{Delta}$$

where the average ratio = $\Sigma(E_t/E_s)/N_e$

Referring once again to FIG. 3, the effects of using such a compensation factor in the calculation of DELTA can be shown. Curve 301 is representative of the stored component values. Curve 302 is representative of the sensed wavelength component values. Curve 303 represents a color signature which is equal to the stored color signature less Delta. Note that the compensated curve is closer to the trained curve then the uncompensated curve.

Figure 2:
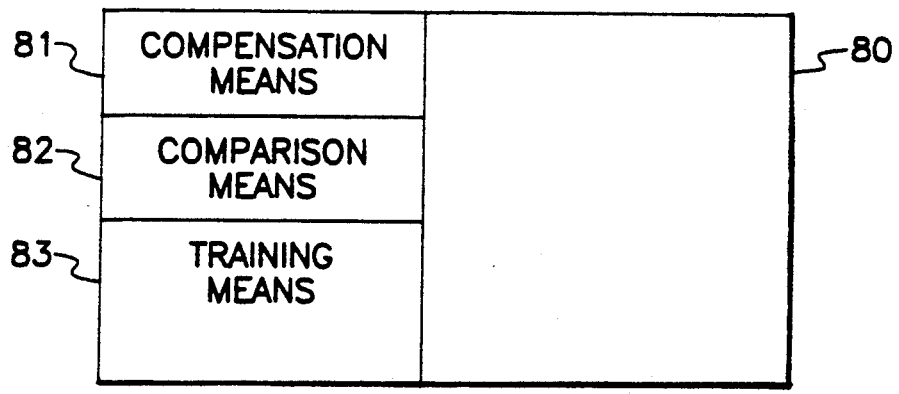
FIG. 2 is a functional diagram of the processor used by the inventive colorimeter.

FIG. 2 shows some parts of processor 80. In FIG. 2, compensation means 81 is used to calculate the correction factor used in the above equations. Comparison means 82 takes the compensation factor, the stored component value and the sensed wavelength component value and produces a DELTA therefrom. Training means 83 is used to create an array of stored component values representative of a color signature. One processor which could be used is an Intel 80C 196 processor.

The foregoing has been a description of a novel and non-obvious colorimeter which provides output compensation for stand off, view angle or lamp paging problems. The inventor does not intend to be limited to only the embodiments shown and described in the application. Instead, the scope of the applicant's invention can be determined by the claims appended hereto.

I claim:

1. Apparatus for determining the acceptability of the color of an object, comprising:
   a lighting means for illuminating the object with light;
   a sensing means in communication with said lighting means for creating an array of sensed component values representative of the intensity of light reflected from the object; and
   a processor having compensation means connected to said lighting means and said sensing means, said processor generating a difference value which is the absolute value of the difference between each of said sensed component values and a product of corresponding stored component values multiplied by an intensity correction factor, said intensity correction factor being equal to the sum of each of said sensed component values divided by a corresponding stored component value, the sum being divided by the number of values.

2. The apparatus of claim 1, wherein:
   said lighting means comprises a lamp and a light focusing means;
   said sensing means comprises a diffraction grating for decomposing reflected light into a predetermined number of components having discrete wavelengths, and an array detector positioned to receive said predetermined number of components and producing a predetermined number of variable electrical signals each of which varies with the intensity of light impinging thereon.

3. The apparatus of claim 2, wherein said light focusing means is comprised of:
   an optical fiber for transmitting light from said lamp to the object; and
   a mirror for reflecting light received from said lamp onto said optical fiber.

4. The apparatus of claim 3, wherein:
   said processor producing an error output if said difference value is outside predetermined limits.

5. The apparatus of claim 3, wherein:
   said processor producing an error output if a sum of said difference values is outside of predetermined limits.

6. Apparatus for determining the acceptability of the color of an object, comprising:
   a lighting means for illuminating the object with light;
   a sensing means in communication with said lighting means and creating an array of sensed component values representative of the intensity of light reflected from the object; and
   a processor having compensation means connected to said sensing means, said processor generating a difference value which is the absolute value of the difference between each value of an array of stored component values and a product of said sensed component values multiplied by an intensity correction factor produced by said compensation means said intensity correction factor being equal to the sum of each of stored component values divided by a corresponding sensed component value, the sum being divided by the number of values.

7. The apparatus of claim 6, wherein:
   said lighting means comprises a lamp and a light focusing means;
   said sensing means comprises a diffraction grating for decomposing reflected light into a predetermined number of components having discrete wavelengths, and an array detector positioned to receive said predetermined number of components and producing a predetermined number of variable electrical signals each of which varies with the intensity of light impinging thereon.

8. The apparatus of claim 7, wherein said light focusing means is comprised of:
   an optical fiber for transmitting light from said lamp to the object; and
   a mirror for reflecting light received from said lamp onto said optical fiber.

9. The apparatus of claim 8, wherein:
   said processor producing an error output if said difference value is outside predetermined limits.

10. The apparatus of claim 8, wherein:
    said processor producing an error output if a sum of said difference values is outside of predetermined limits.

11. A method for determining the acceptability of the color of an object, comprising the steps of:
    illuminating the object;
    sensing reflected light from the object;
    separating the reflected light into sensed component values;
    calculating an intensity correction factor which is equal to the sum of each of the sensed component values divided by a corresponding stored component value, the sum being divided by the number of values; and
    determining a difference value which is the absolute value of the difference between each of said sensed component values and a product of said corresponding stored component values multiplied by said intensity correction factor.

12. The method of claim 11, comprising the further step of:
    generating a first output if all of the difference values are within preselected limits and a second output if any of the difference values is not within a preselected limit.

13. The method of claim 11, comprising the further step of:
    generating a first output if the sum of all of the difference values is within preselected limits and a second output if the sum of the difference values is not within a preselected limit.

14. A method for determining the acceptability of the color of an object, comprising the steps of:
    illuminating the object;
    sensing reflected light from the object;
    separating the reflected light into sensed component values;
    calculating an intensity correction factor which is equal to the sum of each value of an array of stored component values divided by a corresponding value of said sensed component values, the sum being divided by the number of values; and determining a difference value which is the absolute value of the difference between each of said stored component values and a product of a corresponding value of said sensed component values multiplied by said intensity correction factor.

15. The method of claim 14, comprising the further step of:

generating a first output if all of the difference values are within preselected limits and a second output if any of the difference values is not within a preselected limit.

16. The method of claim 14, comprising the further step of:

generating a first output if the sum of all of the difference values is within preselected limits and a second output if the sum of the difference values is not within a preselected limit.

17. An improved apparatus for determining the acceptability of color of an object of the type including a lighting means for lighting the object and a sensing means for creating a sensed component value representative of light received from the object, wherein the improvement comprises:

a processor connected to said sensing means, said processor generating a difference value which is the difference between the sensed component values and a product of a stored component value and an intensity correction factor, said processor further producing an error output if said difference value is outside predetermined limits.

18. An improved apparatus for determining the acceptability of color of an object of the type including a lighting means for lighting the object and a sensing means for creating a sensed component value representative of light received from the object, wherein the improvement comprises:

a processor connected to said sensing means, said processor generating a difference value which is the difference between an array of stored component values and a product of a corresponding sensed component value and an intensity correction factor, said processor further producing an error output if said difference value is outside predetermined limits.

* * * * *